United States Patent [19]

Merger et al.

[11] 4,198,531
[45] Apr. 15, 1980

[54] MANUFACTURE OF P-ALKYLPHENOLS

[75] Inventors: Franz Merger, Frankenthal; Max Strohmeyer, Limburgerhof; Gerhard Sandrock, Frankenthal; Heinz Hohenschutz, Mannheim; Ludwig Schroff; Gerhard Nestler, both of Ludwigshafen, all of Fed. Rep. of Germany

[73] Assignee: BASF Aktiengesellschaft, Fed. Rep. of Germany

[21] Appl. No.: 842,304

[22] Filed: Oct. 14, 1977

Related U.S. Application Data

[63] Continuation of Ser. No. 695,427, Jun. 14, 1976, Pat. No. 4,068,275.

[30] Foreign Application Priority Data

Jun. 14, 1975 [DE] Fed. Rep. of Germany ....... 2526644

[51] Int. Cl.$^2$ .............................................. C07C 39/06
[52] U.S. Cl. ................................................... 568/793
[58] Field of Search ........... 260/624 R, 624 C, 619 R; 568/793

[56] References Cited

U.S. PATENT DOCUMENTS

| | | | |
|---|---|---|---|
| 2,802,884 | 8/1957 | D'Alelio | 260/624 |
| 3,037,052 | 5/1962 | Bortnick | 260/485 |

*Primary Examiner*—Werren B. Lone
*Attorney, Agent, or Firm*—Keil & Witherspoon

[57] ABSTRACT p-alkylphenols are manufactured by continuous reaction of phenol with olefins in the presence of a pulverulent polystyrenesulfonic acid ion exchanger which is suspended in the reaction mixture.

13 Claims, No Drawings

MANUFACTURE OF P-ALKYLPHENOLS

This is a continuation of application Ser. No. 695,427, filed June 14, 1976 now U.S. Pat. No. 4,068,275.

The p-alkylphenols which may be manufactured by the process of the invention are valuable starting materials for the manufacture of dyes, pesticides, pharmaceuticals, emulsifiers, dispersing agents, stabilizers, antioxidants, plasticizers, corrosion inhibitors, disinfectants, seed dressings, anti-aging agents, plant protection agents and perfumes.

The present invention relates to a process for the manufacture of p-alkylphenols by continuous reaction of phenol with olefins in the presence of a pulverulent polystyrenesulfonic acid ion exchanger suspended in the reaction mixture.

Houben-Weyl, Methoden der Organischen Chemie, volume 1/1, page 585–587, discloses that cation exchangers, including sulfonated resins, may be used as catalysts for continuous processes, and points out that the particle size of the resin has a substantial effect on its catalytic activity. In accordance with the disclosure in Houben-Weyl, particles of from 0.5 to 1 mm diameter are therefore advantageously used for batchwise catalytic reactions. By contrast, continuous processes carried out industrially in towers require a particularly coarse material to permit free passage of the reactants. In agreement with this, U.S. Pat. No. 2,802,884 teaches that the alkylation of phenol with alkenes should be carried out continuously only when using sulfonic acid ion exchange resins of coarse particle size, namely from 10 to 20 mesh; the catalyst forms a fixed bed in the reactor.

A continuous reaction using a fixed bed of a porous acid cation exchange resin is also disclosed in German printed application No. 1,443,346; here, the greater part of the reaction mixture formed is recycled and the remainder is reacted again in a further reactor packed with a fixed bed of the same catalyst. The description shows that the catalyst is always packed into the reactor as a fixed bed; the use of fine pulverulent ion exchange resins in suspension is not mentioned.

All these processes are unsatisfactory with regard to yield, simplicity and economy of operation and in particular to dissipation of the large amounts of heat evolved during the reaction.

It is an object of the present invention to provide a novel process by means of which a large number of p-alkylphenols may be manufactured more simply and more economically, with a better space-time yield and in a better purity, specifically on an industrial scale and in continuous operation.

We have found that this object is achieved and that p-alkylphenols of the formula

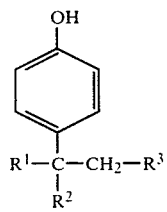

I, where $R^1$, $R^2$ and $R^3$ may be identical or different and each is alkyl, but $R^1$ may also be alkylphenyl or phenyl and $R^2$ and/or $R^3$ may also be hydrogen, are obtained in an advantageous manner in the reaction of phenols with olefins in the presence of cation exchangers, when phenol is reacted continuously with olefins of the formula

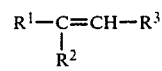

II, where $R^1$, $R^2$ and $R^3$ have the above meanings, in the presence of an organic sulfonic acid cation exchanger, of particle size from 10 to 200 micrometers, which is suspended in the fluid reaction mixture.

Where isobutene is used, the reaction may be represented by the following equation:

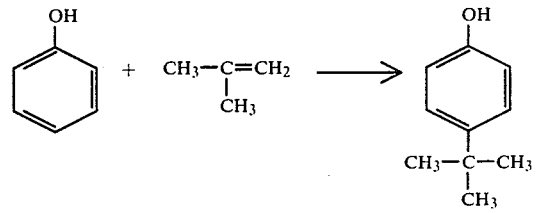

Compared to the conventional processes, the process of the invention gives, surprisingly, a large number of p-alkylphenols more simply and more economically, with better space-time yield and in better purity, and specifically on an industrial scale and in continuous operation. The heat of reaction is dissipated more easily and the use of special cooling devices, and the recycling of the greater part of the reaction mixture, is avoided. Compared to the conventional processes, just one reaction in the presence of the catalyst results in larger amounts of the p-alkyl compound, and expensive separation of mixtures of the o-alkyl compound and the o,p-dialkyl compound, or trans-alkylation in a further process stage, prove unnecessary. Conventional reactor jacket cooling or pipe coil cooling systems suffice. Since lower reaction temperatures can be used, the life of the catalyst is longer and hence the process is more economical. As compared to the disclosure of the German Printed Application, the process of the invention permits the use of lower, and hence of substantially more advantageous, catalyst factors, the factor being defined as dry catalyst (g)/rate of feed (g/hour). The reaction itself takes place more rapidly, and specifically at temperatures below 120° C. All these advantages of the process of the invention are surprising, especially since not only macro-reticular ion exchange resins, but also (advantageously) gel-like ion exchange resins can be used. Regarding the macro-reticular or gel-like structure of resins, reference may be made to German Pat. No. 1,168,908.

Furthermore, the disclosure in Houben-Weyl in itself would already have led to the expectation that the fine pulverulent ion exchange resins of the invention would, in continuous operation, give poorer yields, poorer throughout of reaction mixture and, correspondingly, inadequate dissipation of the heat of reaction and therefore substantially decomposition and polymerization. Furthermore, it is surprising that the catalyst can be removed without the addition of a filtration assistant.

The invention is based on the observation, inter alia, that catalyst particles having a size of from 10 to 200 micrometers can be suspended, by means of a stirrer or mixer, in the continuously flowing reaction mixture in such a way that they are retained, and back-mixed, on a filter device in the reactor without impermeable membranes being formed. No specific type of filter is required. Correspondingly, the losses of catalyst particles are very low. Surprisingly, the process of the invention can be operated for long onstream periods. Breakdowns due to the formation of a film on the filters only occur if the mixer fails and can, if necessary, be remedied by introducing inert gas in counter-current.

The starting material II may be reacted with a stoichiometric amount or an excess of phenol, preferably in a ratio of from 0.3 to 1, especially from 0.5 to 0.75, mole of starting material II per mole of phenol. If a larger excess of starting material II is used, in particular 2 or more than 2, and advantageously from 2 to 3.5, moles of starting material per mole of phenol, increasing amounts of o,p-alkylphenols and/or o,o',p-alkylphenols are formed, as the amount of starting material II increases. Preferred starting materials II and, correspondingly, preferred end products I are those where $R^1$, $R^2$ and $R^3$ may be identical or different and each is alkyl of 1 to 9 carbon atoms and especially of 1 to 4 carbon atoms, $R^1$ may also be alkylphenyl of 7 to 12 carbon atoms or phenyl and $R^2$ and/or $R^3$ may also be hydrogen. The above radicals may also be substituted by groups which are inert under the reaction conditions, eg. alkyl of 1 to 3 carbon atoms. The use of branched alkenes is preferred. In contrast to conventional processes, mixtures of alkenes, or, if appropriate, of alkenes with alkanes, may also be used; such mixtures are obtained, eg., in the cracking or dehydrogenating of hydrocarbons, eg. petroleum, or in the oligomerization of olefins, especially isobutylene, propylene or n-butene, or in the hydrogenation of carbon monoxide.

The following are examples of olefins which may be used as starting materials II: n-pent-1-ene, n-hex-1-ene, n-hept-1-ene, n-oct-1-ene, n-non-1-ene, n-dec-1-ene, N-undec-1-ene, n-dodec-1-ene, propene and n-but-1-ene; the above alkenes substituted by methyl, ethyl, n-propyl, isopropyl, n-butyl, isobutyl, sec.-butyl or tert.-butyl in the 2-, 3- or 4-position; 2,3-dimethyl-n-butene, 3,3-dimethyl-n-butene, 2,5-dimethylheptene, 3,3-dimethylheptene, 2,3,4-trimethylheptene, 2,4-dimethylheptene, 2,3-dimethylheptene, 4,4-dimethylheptene, 2,3-diethylhexene, 4,4-dimethylhexene, 2,3-dimethylhexene, 2,4-dimethylhexene, 2,5-dimethylhexene, 3,3-dimethylhexene, 3,4-dimethylhexene, 2-methyl-3-ethylpentene, 3-methyl-3-ethylpentene, 2,3,3-trimethylheptene, 2,4,4-trimethylpentene, 2,3,3-trimethylpentene, 2,3,4-trimethylpentene and 2,3,3,4-tetramethylpentene; analogous alkenes wherein the double bond is in the 2-position or 3-position of the molecule; branched alkenes as obtained in the form of mixtures, by dimerizing isobutylene or n-butene (octenes) or trimerizing isobutylene or n-butene (dodecenes) or propene (nonenes) or tetramerizing propene (dodecenes); styrene, o-methylstyrene, m-methylstyrene, p-methylstyrene, 3,4-dimethylstyrene, 2,4-dimethylstyrene, 2,5-dimethylstyrene, 2,6-dimethylstyrene, o-ethylstyrene, m-ethylstyrene, p-ethylstyrene, 3,4-diethylstyrene, 2,4-diethylstyrene, 2,5-diethylstyrene, 2,6-diethylstyrene, o-propylstyrene, m-propylstyrene, p-propylstyrene, o-isopropylstyrene, m-isopropylstyrene, p-isopropylstyrene, o-butylstyrene, m-butylstyrene, p-butylstyrene, o-isobutylstyrene, m-isobutylstyrene, p-isobutylstyrene, o-sec.-butylstyrene m-sec.-butylstyrene, p-sec.-butylstyrene, o-tert.-butylstyrene, m-tert.-butylstyrene and p-tert.butylstyrene.

The following are preferred: isobutene, diisobutene, triisobutene, styrene, α-methylstyrene, nonenes and dodecenes obtained by trimerizing and tetramerizing propene, 2,3-dimethylbut-1-ene, 2-methyl-but-1-ene, 2-methyl-but-2-ene, 2-methyl-pent-1-ene, 2-methyl-hex-1-ene, 2-methyl-hept-1-ene, 2,3-dimethyl-pent-1-ene, 2,3-dimethyl-hex-1-ene and 2,4,4-trimethylpent-1-ene.

The reaction is in general carried out continuously at from 70° to 140° C., preferably from 80° to 125° C. and especially from 80° to 120° C., at subatmospheric, superatmospheric or atmospheric pressure, preferably at a pressure of from 1 to 10 bars, especially at from 1 to 3 bars. The residence time is preferably from 0.5 to 20 hours, especially from 1 to 10 hours, and the throughput is preferably from 1 to 120, especially from 5 to 50, kilograms of starting material II per kilogram of catalyst and per hour.

The catalysts are organic sulfonic acid cation exchangers, advantageously resins of sulfonated styrene/divinylbenzene copolymers, sulfonated crosslinked styrene polymers and phenol-formaldehyde or benzene-formaldehyde resins containing sulfonic acid groups. Sulfonated styrene/divinylbenzene copolymer ion exchangers are preferred. The exchangers are in the form of the free acid and not in the form of salts. The particle size of the catalyst is from 10 to 200, preferably from 20 to 180, and especially from 25 to 150, micrometers. Advantageously, the catalyst has a gel-like structure. Examples of suitable catalysts are ion exchange resins commercially available under the name LEWASORB A-10 (a registered tradename). Alternatively, (other) commercially available resins, eg. Amberlite IR-120, Dowex 50, Lewatit S-100, Nalcit HCR, Permutit RS and Wofatit KPS-200 (these being registered tradenames) may be ground to the particle size required according to the invention, and then used. Advantageously, the resins are dehydrated by conventional methods, eg. by heating at 100° C. under reduced pressure, before being used as catalysts. Dehydration may be also be carried out by displacing the water with hydrophilic organic fluids and then heating the product at 100° C. under reduced pressure, or by azeotropic distillation with an organic fluid.

During the reaction, the catalyst is in suspension, as a rule in the reaction mixture which is being formed. An advantageous procedure is first to introduce a part of the fluid phenol or of the starting mixture of phenol and olefin II and to suspend the catalyst in this fluid, with thorough mixing. Although it is advantageous not to add any solvents, solvents which are inert under the reaction conditions may be used, eg. in order to lower the viscosity of the reaction mixture. Examples of suitable solvents are aliphatic or cycloaliphatic hydrocarbons, eg. heptane, nonane, gasoline fractions of boiling range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; halohydrocarbons, particularly chlorohydrocarbons, eg. tetrachloroethylene, 1,1,2,2-tetrachloroethane or 1,1,1,2-tetrachloroethane, dichloropropane, methylene chloride, dichlorobutane, chloroform, carbon tetrachloride, tetrachloroethane, 1,1,1-trichloroethane or 1,1,2-trichloroethane, trichloroethylene, pentachloroethane, cis-dichloroethylene, 1,2,-dichloroethane and 1,1-dichloroethane; tetrahydrofuran and dioxane; and appropriate mixtures. Advantageous amounts of solvent to use are from 10 to 1,000% by weight, preferably from 50 to 100% by weight, based on starting material II. Where mixtures of starting materials II, eg. from the cracking of petroleum, are used, the saturated hydrocarbons present in the mixture may be employed as the solvent for the suspension. The amount of phenol or starting mixture and/or organic solvent is such that the amount of catalyst suspended in the reaction mixture which forms is from 0.3 to 10% by weight, preferably from 1 to 3% by weight, based on the weight of the total fluid mixture in the reactor. Advantageously, the reaction mixture is mixed throughout the entire reaction, preferably by stirring at a speed of at least 300, advantageously from 400 to 2,000, and especially from 500 to 1,000, revolutions per minute. When mixing is not carried out by means of a stirrer, eg. with an inert gas such as nitrogen, devices which introduce a shear energy corresponding to the above stirring speeds are preferred. This results in a finely disperse suspension. Under the above mixing conditions, a broad range of conventional stirring devices may be used, such as injectors, ball jets, vortex jets, turbine stirrers, mixing nozzles, Lechler mixing nozzles, paddle stirrers, anchor stirrers, bar-type stirrers, propeller stirrers, Cramer stirrers, vibro-mixers, fingertype stirrers, crossbeam stirrers, gyratory stirrers, grid stirrers, flat stirrers, spiral turbines, blade mixers, planetary mixers, centrifugal gyratory stirrers, rotating atomizers, ejectors, triangular stirrers, hollow stirrers, tubular stirrers and impeller stirrers. It is also possible to use equipment such as stirred kettles, stirred kettle cascades, flow tubes, air-lift type stirring units, homogenizing equipment, gyratory mixers, emulsifying centrifuges, ultrasonic tubes, flow mixers, rotating drums, chamber reactors, circulatory reactors, loop reactors, cellular reactors, screw reactors, bubble columns, jet scrubbers, liquid ring pumps, ejectortype tubular reactors and thin film reactors; for economic reasons alone, it is preferred to use stirred kettles.

The reaction may be carried out as follows: a fluid mixture of the starting material II and phenol, if desired together with solvent, is passed, at the reaction temperature and the reaction pressure, through a suspension of the catalyst in the starting mixture or in the reaction mixture, and is then filtered. The end product is then isolated from the reaction mixture in a conventional manner, eg. by distillation. Filtration is advantageously carried out before the suspension leaves the reactor. Suitable filters are acid-resistant filter cloths, wire net filters and sintered metal filters, provided the mesh width or pore diameter is smaller than the catalyst particles.

The p-alkylphenols which may be manufactured by the process of the invention are valuable starting materials for the manufacture of dyes, pesticides, pharmaceuticals, emulsifiers, dispersing agents, stabilizers, antioxidants, plasticizers, corrosion inhibitors, disinfectants, seed dressings, anti-aging agents, plant protection agents and perfumes. For details of their use, reference may be made to the above publications, Ullmanns Encyklopadie der technischen Chemie, volume 13, pages 440–447, and Kirk-Othmer, Encyclopedia of Chemical Technology, volume 1, pages 901–916 (2nd edition).

In the Examples which follow, parts are by weight and bear the same relation to parts by volume as that of the kilogram to the liter.

EXAMPLE 1

A suspension of 20 parts of phenol and 0.6 part of ion exchange resin is prepared in a stirred reactor at 85° C. and 1 bar pressure, whilst stirring at 500 rpm, and 7 parts of isobutylene are passed in. The ion exchange resin is a sulfonated styrene/divinylbenzene copolymer resin, which has been dehydrated under reduced pressure for 20 hours at 100° C. before being used; it has a gel structure and its particle size is from 20 to 150 micrometers. The suspension is then stirred constantly in the reactor at 500 rpm. After 6 hours, 2.5 parts of phenol and 380 parts by volume of isobutylene are introduced per hour at 115° C. and 1 bar pressure and correspondingly 3.5 parts per hour of suspension are filtered through a suction line equipped with a metal filter (pore diameter 10 micrometers) and subjected to fractional distillation. After 200 hours' operation, 316 parts (88% of theory, based on starting material II) of 4-tert.-butylphenol of boiling point 143°–145° C./50 millibars are obtained, accompanied by 19.8 parts (5.5% of theory, based on starting material II) of 2-tert.-butylphenol and 9.9 parts (6.5% of theory, based on starting material II) of 2,4-di-tert.-butylphenol. The conversion is 60% of theory, based on phenol employed. The starting material II is consumed practically quantitatively.

EXAMPLE 2

A suspension of 1,000 parts of phenol, 700 parts of diisobutylene and 40 parts of ion exchange resin is prepared in a stirred reactor at 100° C. and 1 bar pressure, the mixture being stirred at 500 rpm. The ion exchange resin is a sulfonated styrene/divinylbenzene copolymer resin, which has been dehydrated under reduced pressure for 20 hours at 100° C. before being used; it has a gel structure and its particle size is from 20 to 150 micrometers. The suspension is then stirred constantly in the reactor at 500 rpm. After 30 minutes, 1,000 parts of phenol and 700 parts of diisobutylene are introduced per hour at 100° C. and 1 bar pressure and correspondingly 1,700 parts per hour of suspension are filtered through a suction line equipped with a metal filter (pore diameter 10 micrometers) and are subjected to fractional distillation. After 100 hours' operation, 116,100 parts (86% of theory, based on starting material II) of 4-tert.-octylphenol of boiling point 160°–162° C./27 millibars are obtained, in addition to 3,400 parts (2.5% of theory, based on starting material II) of 2-tert.-octylphenol and 1,750 parts (0.9% of theory, based on starting material II) of tert.-butylphenol. The conversion is 54%, based on phenol employed, or 91%, based on starting material II.

EXAMPLE 3

A suspension of 190 parts of phenol, 152 parts of propylene trimer and 7 parts of ion exchange resin is prepared in a stirred reactor at 120° C. and 1 bar pressure, the mixture being stirred at 500 rpm. The ion exchange resin is a sulfonated styrene/divinylbenzene copolymer resin, which has been dehydrated under reduced pressure for 20 hours at 100° C. before being used; it has a gel structure and its particle size is from 20 to 150 micrometers. The suspension is then stirred constantly in the reactor at 500 rpm. After 6 hours, 12.1 parts of phenol and 9.8 parts of propylene trimer are introduced per hour at 120° C. and 1 bar pressure and correspondingly 21.9 parts per hour of suspension are filtered through a suction line equipped with a metal filter (pore diameter 10 micrometers) and are subjected to fractional distillation. After 200 hours' operation, 3,145 parts (92% of theory, based on starting material II) of 4-nonylphenol of boiling point 175°–180° C./27 millibars are obtained. The conversion is 57%, based on phenol employed, or 95% based on starting material II.

EXAMPLE 4

A suspension of 200 parts of phenol, 234 parts of propylene trimer and 15 parts of ion exchange resin is prepared in a stirred reactor at 120° C. and 1 bar pressure, the mixture being stirred at 700 rpm. The ion exchange resin is a sulfonated styrene/divinylbenzene copolymer resin, which has been dehydrated under reduced pressure for 20 hours at 100° C. before being used; it has a gel structure and its particle size is from 20 to 150 micrometers. The suspension is then stirred constantly in the reactor at 700 rpm. After 8 hours, 10 parts of phenol and 16.7 parts of propylene trimer are introduced per hour at 120° C. and 1 bar pressure and correspondingly 26.7 parts per hour of suspension are filtered through a suction line equipped with a metal filter (pore diameter 10 micrometers). After 200 hours' operation, 3,070 parts (84% of theory, based on starting material II) of 4-dodecylphenol of boiling point 152°–156° C./1 millibar are obtained. The conversion is 55% of theory, based on phenol employed, or 85%, based on starting material II.

EXAMPLE 5

A suspension of 188 parts of phenol, 125 parts of styrene and 5 parts of ion exchange resin is prepared in a stirred reactor at 80° C. and 1 bar pressure, the mixture being stirred at 700 rpm. The ion exchange resin is a sulfonated styrene/divinylbenzene copolymer resin, which has been dehydrated under reduced pressure for 20 hours at 100° C. before being used; it has a gel structure and its particle size is from 20 to 150 micrometers. The suspension is then stirred constantly in the reactor 700 rpm. After 3 hours, 24.4 parts of phenol and 16.2 parts of styrene are introduced per hour at 80° C. and 1 bar pressure and correspondingly 40.6 parts per hour of suspension are filtered through a suction line equipped with a metal filter (pore diameter 10 micrometers) and are subjected to fractional distillation. After 100 hours' operation, 2,840 parts (92% of theory, based on starting material II) of 4-(α-phenylethyl)-phenol of boiling point 136°–139° C./4 millibars are obtained, in addition to 155 parts (5% of theory, based on starting material II) of 2-(α-phenylethyl)-phenol and 47.2 parts (2% of theory, based on starting material II) of di-(α-phenylethyl)-phenol. The conversion is 59% of theory, based on phenol employed, or practically 100%, based on starting material II.

EXAMPLE 6

A suspension of 94 parts of phenol, 208 parts of styrene and 5 parts of ion exchange resin is prepared in a stirred reactor at 80° C. and 1 bar pressure, the mixture being stirred at 700 rpm. The ion exchange resin is a sulfonated styrene/divinylbenzene copolymer resin, which has been dehydrated under reduced pressure for 20 hours at 100° C. before being used; it has a gel structure and its particle size is from 20 to 150 micrometers. The suspension is then stirred constantly in the reactor at 700 rpm. After 10 hours, 4.7 parts of phenol and 10.4 parts of styrene are introduced per hour at 80° C. and 1 bar pressure and correspondingly 15.1 parts per hour of suspension are filtered through a suction line equipped with a metal filter (pore diameter 10 micrometers) and are subjected to fractional distillation. After 100 hours' operation, 248 parts of 4-mono-(α-phenylethyl)-phenol (13% of theory, based on starting material II) of boiling point 182°–189° C./13 millibars, 845 parts (56% of theory, based on starting material II) of 2,4-di-(α-phenylethyl)-phenol of boiling point 231°–235° C./6 millibars and 366 parts (27% of theory, based on starting material II) of 2,4,6-tri-(α-phenylethyl)-phenol of boiling point 260°–268° C./6 millibars are obtained. The conversion is 98%, based on phenol, or 97%, based on starting material II.

EXAMPLE 7

A suspension of 188 parts of phenol, 84 parts of a mixture of 85% of 2-methylbut-1-ene and 15% of 2-methylbut-2-ene and 7 parts of ion exchange resin is prepared in a stirred reactor at 100° C. and 1.5 bars pressure, the mixture being stirred at 500 rpm. The ion exchange resin is a sulfonated styrene/divinylbenzene copolymer resin, which has been dehydrated under reduced pressure for 20 hours at 100° C. before being used; it has a gel structure and its particle size is from 20 to 150 micrometers. The suspension is then stirred constantly in the reactor at 500 rpm. After 2 hours, 37 parts of phenol and 17 parts of starting material II are introduced per hour at 100° C. and 1.5 bars pressure and correspondingly 54 parts per hour of suspension are filtered through a suction line equipped with a metal filter (pore diameter 10 micrometers) and are subjected to fractional distillation. After 100 hours' operation, 3,681 parts (92.5% of theory, based on starting material II) of 4-tert.-amylphenol of boiling point 147°–149° C./30 millibars are obtained, in addition to 136 parts (3.4% of theory, based on starting material II) of 2-tert.-amylphenol and 56 parts (1% of theory, based on starting material II) of di-tert.-amylphenol. The conversion is 59.5%, based on phenol employed, and 97%, based on starting material II.

We claim:
1. In a process for the continuous manufacture of p-alkylphenols of the formula

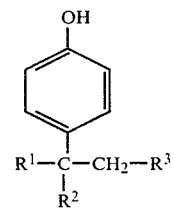

where $R^1$ is selected from the group consisting of alkyl of 1 to 9 carbon atoms, phenol and alkylphenol and $R^2$ and $R^3$ may be identical or different and each is hydrogen or alkyl of 1 to 9 carbon atoms, in which phenol and an olefin of the formula

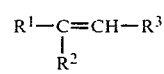

where $R^1$, $R^2$ and $R^3$ have the above meanings are continuously added to a reaction mixture maintained in a reaction zone at a temperature of from about 70° to 140° C., said reaction zone containing a fixed bed of an organic sulfonic acid cation exchanger having a particle size of from 10 to 20 mesh, wherein the improvement comprises:

replacing said fixed bed catalyst with a catalyst which is suspended in the reaction mixture, using an organic sulfonic acid cation exchanger which has a particle size of from 10 to 200 micrometers, stirring said reaction mixture at a speed of from about 400 to 2,000 rpm, and continuously withdrawing reaction product I from the reaction mixture while retaining the catalyst particles suspended within the reaction zone.

2. A process as claimed in claim 1, wherein the reaction mixture is mixed throughout the reaction by stirring at from 500 to 1,000 rpm.

3. A process as claimed in claim 1, wherein the reaction is carried out with from 0.3 to 1 mole of starting material II per mole of phenol.

4. A process as claimed in claim 1, wherein the reaction is carried out at from 80° to 125° C.

5. A process as claimed in claim 1, wherein the reaction is carried out at a pressure of from 1 to 10 bars.

6. A process as claimed in claim 1, wherein the reaction is carried out with a residence time of from 0.5 to 20 hours.

7. A process as claimed in claim 1, wherein the reaction is carried out with a throughput of from 1 to 120 kilograms of starting material II per kilogram of catalyst and per hour.

8. A process as claimed in claim 1, wherein the reaction is carried out with sulfonated styrene/divinylbenzene copolymer ion exchange resins.

9. A process as claimed in claim 1, wherein the reaction is carried out with a catalyst having a particle size of from 20 to 180 micrometers.

10. A process as claimed in claim 1, wherein the reaction is carried out with a catalyst having a particle size of from 25 to 150 micrometers.

11. A process as claimed in claim 1, wherein the reaction is carried out with a catalyst having a gel-like structure.

12. A process as claimed in claim 1, wherein the reaction is carried out in the presence of a solvent used in an amount of from 10 to 1,000% by weight, based on starting material II.

13. A process as claimed in claim 1, wherein the reaction is carried out with a catalyst, suspended in the reaction mixture being formed, in an amount of from 0.3 to 10% by weight, based on the weight of the total fluid mixture in the reactor.

* * * * *